United States Patent
Stridfeldt et al.

(10) Patent No.: US 10,159,612 B2
(45) Date of Patent: Dec. 25, 2018

(54) ABSORBENT PRODUCT COMPRISING ODOR CONTROL MATERIAL

(71) Applicant: SCA Hygiene Products AB, Göteborg (SE)

(72) Inventors: Chatrine Stridfeldt, Göteborg (SE); Pia Kalentun, Göteborg (SE); Ulla Forsgren Brusk, Göteborg (SE); Barbro Moberg, Göteborg (SE); Frida Ryttsén, Göteborg (SE); Birgitta Yhlen, Göteborg (SE)

(73) Assignee: ESSITY HYGIENE AND HEALTH AB, Göteborg (SE)

( * ) Notice: Subject to any disclaimer, the term of this patent is extended or adjusted under 35 U.S.C. 154(b) by 305 days.

(21) Appl. No.: 15/104,119

(22) PCT Filed: Dec. 20, 2013

(86) PCT No.: PCT/SE2013/051603
§ 371 (c)(1),
(2) Date: Jun. 13, 2016

(87) PCT Pub. No.: WO2015/094068
PCT Pub. Date: Jun. 25, 2015

(65) Prior Publication Data
US 2017/0027778 A1 Feb. 2, 2017

(51) Int. Cl.
*A61F 13/532* (2006.01)
*A61F 13/537* (2006.01)
(Continued)

(52) U.S. Cl.
CPC .... *A61F 13/8405* (2013.01); *A61F 13/15577* (2013.01); *A61F 13/53743* (2013.01);
(Continued)

(58) Field of Classification Search
CPC .. A61F 2013/530861; A61F 2013/8408; A61F 2013/842; A61F 13/53747
See application file for complete search history.

(56) References Cited

U.S. PATENT DOCUMENTS

| | | | |
|---|---|---|---|
| 3,340,875 A | 9/1967 | Dudley | |
| 4,992,326 A | 2/1991 | Dabi | |

(Continued)

FOREIGN PATENT DOCUMENTS

| | | | |
|---|---|---|---|
| CN | 101304770 A | 11/2008 | |
| CN | 101325981 A | 12/2008 | |

(Continued)

OTHER PUBLICATIONS

Office Action dated Jul. 19, 2016, by the Colombian Patent Office in Colombian Patent Application No. NC2016/0000059, and an English Translation of the Office Action. (25 pages).

(Continued)

*Primary Examiner* — Susan S Su
(74) *Attorney, Agent, or Firm* — Buchanan Ingersoll & Rooney P.C.

(57) ABSTRACT

Hygienic product comprising an odor control material having a longitudinal direction, a transverse direction and a thickness direction, the odor control material including a first carrier material wherein a plurality of odor control particles are bonded to at least one surface of the first carrier material by a binder substance wherein the first carrier material in an unexpanded condition has a plurality of transversal slits, and that the first carrier material in an expanded condition in the longitudinal direction has a plurality of openings, and that the first carrier material is fixed in the expanded condition in the hygienic product whereby the odor control material is in the form of a reticulated structure.

11 Claims, 4 Drawing Sheets

(51) Int. Cl.
*A61F 13/15* (2006.01)
*A61F 13/84* (2006.01)
*A61L 15/46* (2006.01)
*A61F 13/53* (2006.01)

(52) U.S. Cl.
CPC .. *A61F 13/53747* (2013.01); *A61F 13/53752* (2013.01); *A61L 15/46* (2013.01); *A61F 2013/530861* (2013.01); *A61F 2013/842* (2013.01); *A61F 2013/8408* (2013.01); *A61F 2013/8411* (2013.01); *A61F 2013/8423* (2013.01)

(56) References Cited

U.S. PATENT DOCUMENTS

| | | | |
|---|---|---|---|
| 5,161,686 | A | 11/1992 | Weber et al. |
| 5,397,316 | A * | 3/1995 | LaVon ................. A61F 13/535 604/358 |
| 5,407,442 | A | 4/1995 | Karapasha |
| 6,025,319 | A | 2/2000 | Surutzidis et al. |
| 6,313,371 | B1 | 11/2001 | Conant et al. |
| 6,344,036 | B1 | 2/2002 | Ivansson |
| 6,479,150 | B1 | 11/2002 | Liu et al. |
| 8,168,852 | B2 | 5/2012 | Quincy, III |
| 9,801,765 | B2 | 10/2017 | Forsgren Brusk et al. |
| 2004/0018359 | A1 | 1/2004 | Haggquist |
| 2004/0121681 | A1 | 6/2004 | Lindsay et al. |
| 2004/0122388 | A1 | 6/2004 | McCormack et al. |
| 2004/0266302 | A1 | 12/2004 | DiSalvo et al. |
| 2006/0142709 | A1 | 6/2006 | Quincy, III |
| 2007/0073255 | A1 | 3/2007 | Thomas et al. |
| 2008/0200890 | A1 | 8/2008 | Wood et al. |
| 2008/0251081 | A1 | 10/2008 | Claussen et al. |
| 2009/0155508 | A1 | 6/2009 | Chau et al. |
| 2011/0130736 | A1 * | 6/2011 | Tsang ................. A61F 13/49017 604/378 |
| 2012/0145008 | A1 | 6/2012 | Chau et al. |
| 2013/0164334 | A1 * | 6/2013 | Quincy, III ......... A61F 13/8405 424/400 |
| 2014/0243768 | A1 * | 8/2014 | Sa ........................ A61L 15/46 604/359 |
| 2014/0295134 | A1 * | 10/2014 | Wood ................. B01J 20/28054 428/135 |
| 2015/0290052 | A1 | 10/2015 | Forsgren Brusk et al. |
| 2017/0027779 | A1 | 2/2017 | Stridfeldt et al. |

FOREIGN PATENT DOCUMENTS

| | | |
|---|---|---|
| CN | 102046213 A | 5/2011 |
| EP | 0 304 952 A2 | 3/1989 |
| EP | 0 389 023 A2 | 9/1990 |
| EP | 0 392 528 A2 | 10/1990 |
| EP | 2 110 018 A1 | 10/2009 |
| FR | 2 462 902 A1 | 2/1981 |
| GB | 2 055 586 A | 3/1981 |
| JP | S48-020296 U | 3/1973 |
| JP | S48-072800 U | 9/1973 |
| JP | S49-118299 U | 9/1974 |
| JP | S 64-83264 A | 3/1989 |
| JP | H08-508424 A | 9/1996 |
| JP | 2008-142464 A | 6/2008 |
| JP | 2009-155734 A | 7/2009 |
| JP | 2010-088530 A | 4/2010 |
| RU | 2 360 406 C1 | 7/2009 |
| WO | 91/12029 A1 | 8/1991 |
| WO | 94/22501 A1 | 10/1994 |
| WO | 97/01317 A1 | 1/1997 |
| WO | WO 98/01300 A1 | 1/1998 |
| WO | WO 98/41607 | 9/1998 |
| WO | WO 99/39675 A1 | 8/1999 |
| WO | WO 2004/006967 A1 | 1/2004 |
| WO | WO 2007/067111 A1 | 6/2007 |
| WO | WO 2007/067112 A1 | 6/2007 |
| WO | 2010/119272 A1 | 10/2010 |
| WO | WO 2012/163995 A1 | 12/2012 |

OTHER PUBLICATIONS

Office Action (Notice of Reasons for Rejection) dated Aug. 21, 2017, by the Japanese Patent Office in Japanese Patent Application No. 2016-541025, and an English Translation of the Office Action. (13 pages).
Office Action dated Sep. 4, 2017, by the Colombian Patent Office in corresponding Colombian Patent Application No. NC2016/0000059, and an English Translation of the Office Action. (19 pages).
Office Action (Notice of Reasons for Rejection) dated Sep. 4, 2017, by the Japanese Patent Office in corresponding Japanese Patent Application No. 2016-540966, and an English Translation of the Office Action. (10 pages).
Office Action dated Oct. 6, 2017, by the Russian Patent Office in corresponding Russian Patent Application No. 2016129457/12(045773). (3 pages).
Office Action dated Jul. 6, 2017, by the Russian Patent Office in Russian Patent Application No. 2015122649/15(035409) and an English Translation of the Office Action. (11 pages).
The extended European Search Report dated Jun. 29, 2017, by the European Patent Office in corresponding European Patent Application No. 13899538.6-1308. (8 pages).
The extended European Search Report issued on Jul. 20, 2017, by the European Patent Office in European Patent Application No. 13899550.1-1453. (7 pages).
Office Action dated Feb. 17, 2017, by the Russian Patent Office in corresponding Russian Patent Application No. 2015122649/15(035409) and an English Translation of the Office Action. (10 pages).
Office Action dated Mar. 28, 2017, by the Colombia Patent Office in corresponding Colombian Patent Application No. 15134574. (11 pages).
Office Action (Decision of Rejection) dated Feb. 6, 2017, by the Japanese Patent Office in Japanese Patent Application No. 2015-541740, and an English Translation of the Office Action. (9 pages).
International Search Report (PCT/ISA/210) dated Jul. 17, 2013, by the European Patent Office as the International Searching Authority for International Application No. PCT/SE2012/051229.
Written Opinion (PCT/ISA/237) dated Jul. 17, 2013, by the European Patent Office as the International Searching Authority for International Application No. PCT/SE2012/051229.
International Preliminary Report on Patentability (PCT/IPEA/409) dated Dec. 4, 2014 for International Application No. PCT/SE2012/051229.
Chinese Office Action dated Nov. 25, 2015 for Application No. 201280076983.6 with English language translation, pp. 1-2.
International Search Report (PCT/ISA/210) dated Sep. 8, 2014, by the European Patent Office as the International Searching Authority for International Application No. PCT/SE2013/051603.
Written Opinion (PCT/ISA/237) dated Sep. 8, 2014, by the European Patent Office as the International Searching Authority for International Application No. PCT/SE2013/051603.
Written Opinion of the International Preliminary Examining Authority (PCT/IPEA/408) dated Dec. 7, 2015, by the European Patent Office for International Application No. PCT/SE2013/051603.
International Preliminary Report on Patentability (PCT/IPEA/409) dated Mar. 3, 2016, by the European Patent Office for International Application No. PCT/SE2013/051603.
International Search Report (PCT/ISA/210) dated Sep. 5, 2014, by the European Patent Office as the International Searching Authority for International Application No. PCT/SE2013/051602.
Written Opinion (PCT/ISA/237) dated Sep. 5, 2014, by the European Patent Office as the International Searching Authority for International Application No. PCT/SE2013/051602.
Written Opinion of the International Preliminary Examining Authority (PCT/IPEA/408) dated Nov. 25, 2015, by the European Patent Office for International Application No. PCT/SE2013/051602.

(56) References Cited

OTHER PUBLICATIONS

International Preliminary Report on Patentability (PCT/IPEA/409) dated Feb. 9, 2016, by the European Patent Office for International Application No. PCT/SE2013/051602.
European Search Report dated Jun. 13, 2016 for Application No. P41105378EP00.
Notice of Allowance dated Oct. 30, 2017, by the Federal Service for Intellectual Property in Russian Patent Application No. 2016129457/12(045773), and an English Translation of the Office Action. (15 pages).
Office Action (Decision to Grant a Patent) dated Mar. 26, 2018, by the Japanes Patent Office in corresponding Japanese Patent Application No. 2016-540966, and an English Translation of the Office Action. (6 pages).

* cited by examiner

ABSORBENT PRODUCT COMPRISING ODOR CONTROL MATERIAL

TECHNICAL FIELD

The present invention relates to an absorbent product comprising an odor control material wherein the odor control material has a longitudinal direction (Y), a transverse direction (X) and a thickness direction (Z). The odor control material comprises a first carrier material with a plurality of odor control particles bonded to the first carrier material by a binder substance.

BACKGROUND

Odor prevention in connection with the use of absorbent products, such as incontinence products, is an important comfort factor for consumers. Bodily fluid, such as urine, is collected and stored in absorbent products and odors may easily arise. It is important for the wearer that these odors do not spread into the environment. The wearer needs to feel safe when using absorbent products both in respect of leakage and odor prevention or control.

In the field of absorbent products, several different solutions are used to prevent odors. For example, odors can be masked by the use of perfumes or deodorizing compounds. Odors may also be adsorbed or absorbed to particles having a large surface area, such as activated carbon, zeolite and starch-based particulate materials. Acidic and/or alkaline odors may be neutralized by the use of substances like baking soda and/or citric acid. For bacteria inhibition, substances having low pH or metal salts can be used. Accordingly, different odor control agents may be used to prevent odors in different manners.

Odor control agents in particle form, such as activated carbon, zeolite and starch-based materials, have been proved to have excellent odor-adsorbing characteristics due to the large surface area of the particles. However, there are some drawbacks related to the use of such odor control agents which may be in a powder form, for example, such powders are very difficult to handle in dry processes due to dusting problems. Powders may contaminate both process equipment and products.

In the prior art, there have been attempts to decrease dusting problems of powders as for example disclosed by EP0392528, in which particles of an odor control agent is bond to a fibrous base web, such as non-woven or paper web. The porous base web is dipped in a saturated slurry containing the odor-absorbing particles and a binding agent, together with a surfactant. The excess slurry is then squeezed from the web and the web is dried.

Odor control agents in particle form may also be difficult to disperse in an even manner in the absorbent products. For example, humidity of the atmosphere may cause the particles to build lumps, and this may cause an uneven distribution in the production process and consequently in final products.

Since certain odor adsorbing particles such as for example activated carbon particles are hydrophobic it is also important that these particles do not impair the absorption properties in the product.

Thus, there is still a need to improve the handling of odor control agents in particle form during the production of absorbent products and also a need to secure that the odor adsorbing/absorbing properties as well as the liquid absorption properties are maintained or improved.

DESCRIPTION OF THE INVENTION

It is an object of the present invention to provide an absorbent product having an efficient odor control system. It is a further object of the present invention to improve the distribution of the odor control particles in the final products so that an efficient odor control system can be obtained without impairing the absorption properties in the final product. It is a further object of the present invention to improve the handling of odor control particles in the production process.

The objects are achieved by an hygienic product comprising an odor control material having a longitudinal direction (Y), a transverse direction (X) and a thickness direction (Z), wherein the odor control material comprising a first carrier material wherein a plurality of odor control particles are bonded to the first carrier material by a binder substance. Furthermore, the first carrier material has in an unexpanded condition a plurality of transversal slits, and in an expanded condition in the longitudinal direction (Y) a plurality of openings. The first carrier material is fixed in the expanded condition in the hygienic product whereby the odor control material is in the form of a reticulated structure. The openings in the material allows the liquid to pass through the material and in that way a hydrophobic character of the odor control particles may not harm the liquid inlet.

Since the carrier material is slitted and fixed in an expanded (stretched) position so that the slits are forming openings, the material is liquid permeable. Thereby it is possible to have the odor control material in close contact to the area where the liquid enters the hygienic product, and it is possible for the odor control particles to immediately capture/adsorb smelling compounds. The odor control material may cover the wetting area of the hygienic product and the odor control material will easier let through liquid. An alternative way of creating openings in a material would be to punch/perforate. However, a slitting method is advantageous over punching/perforating since no material is cut out from the web. This saves money due to less waste of material and also improves the handling in the production process by avoiding to handle a lot of small pieces comprising odor control particles. These small pieces of material may otherwise contaminate both the process equipment and the final product.

The odor control particles may be activated carbon, zeolite or a starch based particulate odor control agent. Activated carbon is a hydrophobic odor control agent, whereby it may adsorb hydrophobic odorous substances while aqueous solutions, such as urine, will pass the particles of activated carbon without absorption of liquid. Activated carbon can be made from a wide range of source materials such as coal, coconut shells and wood. The material is often charred to achieve carbon, followed by chemical activation or activation by high temperature steam. This produces an activated carbon with an extensive network of pores and a high surface area.

The particles of the activated carbon may have a particle size of from about 0.1-1000 μm and is preferably from about 1 μm to about 250 μm, measured according to ASTM D5158. Particles having a size smaller than 0.1 μm are often difficult to handle. On the other hand, particles which are larger than 250 μm may feel uncomfortable or uneven in the final product such as the absorbent product. The specific surface area of the particles determines the area of the substance that is available for binding of and/or interaction with other substances. The specific surface area is defined as BET-surface area. The BET-theory describes the adsorption of gas molecules to a solid surface and is based upon an assumption for the energy for the adsorption of the first layer. By measuring the volume of the gas after desorption, the specific surface area is calculated. The skilled person would know conventional instruments for performing the measurement.

Generally, the BET-specific surface area of the water-insoluble particles of activated carbon used in the present invention may be from 100 $m^2/g$ to 2000 $m^2/g$ and is preferably larger than 500 $m^2/g$. The specific surface area depends on the physical properties of the particles.

According to one embodiment, the first carrier material is fixed in the expanded condition in the hygienic product so that the odor control material covers 5-100% of the total surface area of the absorbent product in its horizontal plane. According to another embodiment, the odor control material may cover 5-60% of the total surface area of the absorbent product in its horizontal plane. When measuring the surface area of the absorbent product covered by odor control material, the total surface area of the odor control material in its expanded condition has been measured which includes the area for the openings. FIG. 2A shows an example of an absorbent product according to an embodiment of the invention, seen from the side which will be facing the user when it is worn. The total surface of the absorbent product in its horizontal plane is for the absorbent product illustrated in FIG. 2A the same as the total surface seen from the side which will be facing the user when worn.

If the hygienic product is an absorbent product such as an incontinence pad or a sanitary napkin, the odor control material may at least be located in the fluid receiving area. If the absorbent product instead is a diaper suitable for absorbing also runny feces, the odor control material may at least be located in the fecal receiving area which is the area that immediately surrounds the point of the absorbent product that is positioned opposite to the user's anus. The fecal receiving area is located in the rear portion of the diaper. So, in a diaper the odor control material may be positioned such that it is only located in the rear portion or in both the rear portion and the front portion.

The first carrier material may be any kind of material such as a foam material or a fibrous material as well as a film material. If the first carrier material is a thin structure, for example a film or a nonwoven, the edges of the slits will be lifted as the material is stretched transversely to the longitudinal direction of the slits, so that the material will transform from a two-dimensional structure to a three-dimensional network structure in which the widened slits form rhomboidal openings. Since the edges of the openings will be located in different planes, an open structure is obtained in which a free volume is present. Due to the free volume, the material may be able to accommodate and temporarily hold a relatively large liquid volume. The openings thus maintain a wide open area which is an advantage for the liquid intake and also for the temporarily holding capacity.

An advantage with a foam as the first carrier material is that foam may be flexible and resilient and therefore such material is comfortable to wear close to the body.

According to one embodiment the slits are provided in staggered rows extending in the transverse direction (X), having a slit length A of 5-20 mm and a slit distance B between the ends of two mutually sequential slits in the staggered row of 0.4-0.6 times the slit length, and a row distance C between two adjacent rows of 0.4-0.6 times the slit length. The slit length A, divided with the row distance C, may be less or equal to 10.

According to one embodiment, the binder substance is water soluble so it at least partially dissolves when in contact with an aqueous solution. By water-soluble binder is meant a binder which is capable of dissolving when in contact with water or an aqueous solution, such as urine or blood. The water-soluble binder substance dissolves partly or completely when it comes in contact with aqueous solutions so that water-insoluble odor control particles adhered to the carrier material with the water-soluble binder substance are released from the binder substance and the carrier material. Thereby, the water-insoluble odor control particles more easily can come into contact with odorous substances. In such a way the whole surface area of the activated carbon particles are utilized for odor adsorption. According to one embodiment has the water-soluble binder substance a molecular weight of 40 kDa or lower.

The water-soluble binder may comprise a hydrophilic polymer such as polyvinylpyrrolidone, polyethyleneoxide polyacrylics, starch or derivatives of starch.

The water-soluble binder may comprise hydrophilic low molecular weight compounds such as monosaccharides such as glucose or similar, disaccharides such as sucrose or similar, sugar alcohols such as xylitol or similar or polyols such as polyethylene glycol or similar.

The water-soluble binder may also comprise a mixture of a hydrophilic polymer such as polyvinylpyrrolidone, polyethyleneoxide polyacrylics, starch or derivatives of starch and low molecular weight compounds such as monosaccharides such as glucose or similar, disaccharides such as sucrose or similar, sugar alcohols such as xylitol or similar or polyols such as polyethylene glycol or similar.

The hygienic product may also comprise an additive such as a plasticizer, stabilizer, agent improving dispersibility, pH regulating agent, antimicrobial substance, perfume and/or scenting substance or a mixture thereof.

According to one embodiment is the hygienic product an absorbent product such as a diaper, sanitary napkin, incontinence protector or a pantyliner. The absorbent product may comprise a liquid permeable top sheet, a liquid impermeable back sheet, and an absorbent core enclosed between the top sheet and the back sheet, and an odor control material located between the topsheet and the absorbent core.

According to one embodiment, the first carrier has a first surface facing the liquid permeable topsheet and a second opposite surface facing the absorbent core wherein the odor control particles are bonded to the second surface which is facing the absorbent core. By this arrangement, the surface of the carrier material with the odor control particles adhered to it is facing the absorbent core and the surface having no odor control particles adhered to it is facing the topsheet. If the odor control particles are activated carbon particles, the dark color of the carbon particles may not be shown through the carrier material if the carrier material is relatively opaque. One example of a carrier material that may be relatively opaque is a foam material.

According to yet another embodiment, the first carrier material is laminated to a second carrier material in its expanded condition so that the first carrier material is fixed to the second carrier material in its expanded condition in the form of a reticulated structure with openings. An advantage by laminating a second carrier material to the first carrier material, is that the first carrier material is locked in its expanded condition after slitting so that the openings formed during the stretching are fixed in its open condition. The second carrier material is for example a nonwoven. The second carrier material may be facing the topsheet and the first carrier material with the carbon particles bonded to it may be facing the absorbent core. It is also possible that the second carrier material in the odor control material is the topsheet, or, if the topsheet comprises more than one layer, at least one layer of the topsheet.

Examples of absorbent products are diapers, incontinence protectors, sanitary napkins, pantyliners. Also non liquid absorbing products such as hygienic products for flatulence are covered in this invention. The hygienic product may also be an insert comprising the odor control material. The insert may be absorbent or non-absorbent.

One way of producing an odor control material of the invention comprises the following steps:

provide a first carrier material having a first surface and a second opposite surface apply a binder substance comprising activated carbon particles on at least one surface of the first carrier material, whereby the carbon particles are adhered to the first carrier material by the binder substance said first carrier material having a longitudinal direction, a transverse direction and a thickness direction;

provide a multitude of transversal slits in said first carrier material, each slit extending through the material in said thickness direction;

expand said first carrier material in said longitudinal direction such that the slits are opened to openings for providing liquid inlet, whereby said expansion provides an expanded first carrier material in the form of a reticulated structure, provide a second carrier material for fixing said expanded first web such that it is maintained in an expanded condition, and laminating said first expanded carrier material and said second carrier material, whereby said expanded first carrier material is fixed in an expanded condition in relation to said second carrier material, and whereby a laminate web of an odor control material is formed.

and cut said odor control material along at least one cutting line, whereby said material piece is produced such that it comprises a plurality of said openings.

Thereafter the odor control material is provided to the absorbent core so that the first carrier material of the odor control material is located towards the absorbent core and the second carrier material is located towards a liquid permeable topsheet. It is also possible that the second carrier material is the topsheet, or, if the topsheet comprises more than one layer, is one layer of the topsheet.

SHORT DESCRIPTION OF FIGURES

DETAILED DESCRIPTION OF THE FIGURES

Figure 1A:
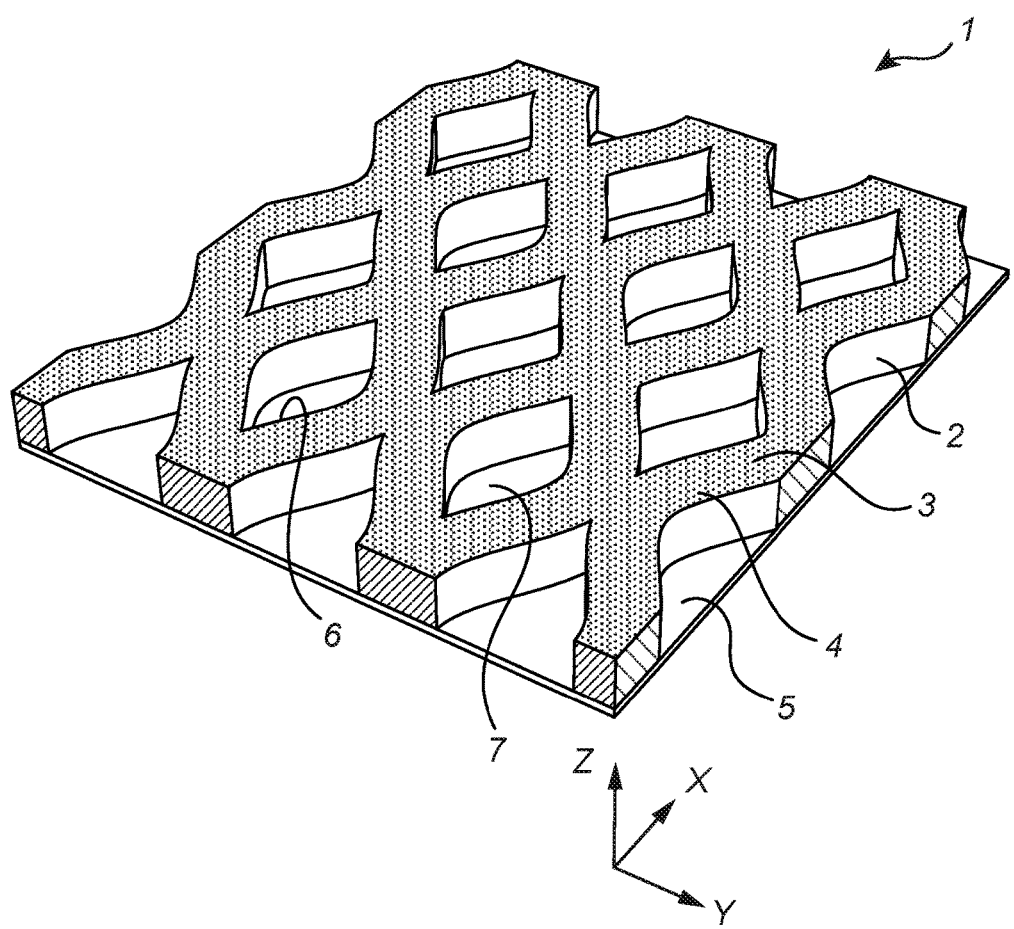
FIG. 1A shows a top view of an odor control material according to an embodiment of the invention.

The invention will now be described by means of examples referring to FIG. 1A-C and FIG. 2A-B. FIG. 1A shows an odor control material 1 according to an embodiment of the invention. The odor control material 1 has a longitudinal direction (Y), a transverse direction (X) and a thickness direction (Z). The odor control material 1 has a first carrier material 2 with a plurality of odor control particles 3 bonded to this first carrier material 2 by a binder substance 4. The odor control particles 3 may be activated carbon, zeolite or a starch based particulate odor control agent. The first carrier material 2 has a plurality of transversal slits 6 and the first carrier material 2 is expanded in the longitudinal direction (Y) so that the slits 6 are opened to openings 7 so that the first carrier material 2 with the plurality of odor control particles 3 is in the form of a reticulated structure. The odor control material 1 in FIG. 1A also has a second carrier material 5 laminated to the first carrier material 2 in its expanded condition so that the first carrier material 2 is fixed to the second carrier material 5 in its expanded condition in the form of a reticulated structure with openings.

Figure 1B:
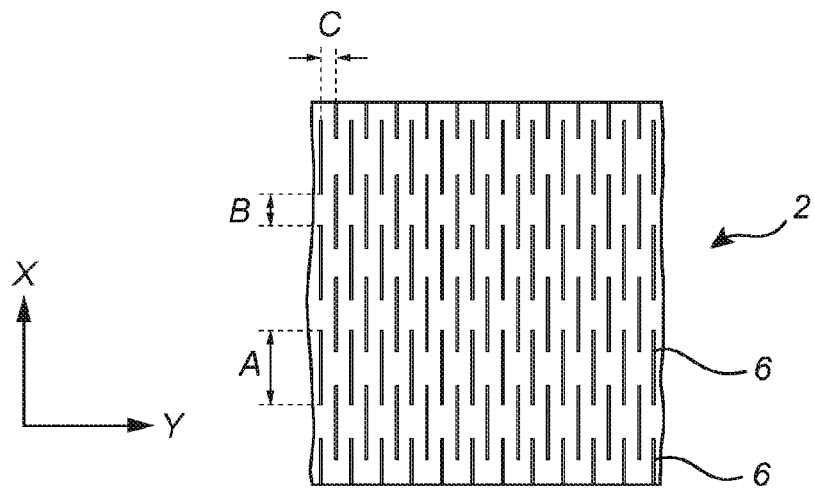
FIG. 1B shows a top view of a portion of an example of a first carrier material after it has been slitted.

FIG. 1B shows a top view of a portion of the first carrier material 2 after provision of transversal slits 6. The slits 6 in FIG. 1B are straight, but may have any suitable shape such as for example wave-shaped. The slits 6 are provided in staggered rows extending in the transverse direction (X), having a slit length A of 5-20 mm and a slit distance B between the ends of two mutually sequential slits in the staggered row of 0.4-0.6 times the slit length A, and a row distance C between two adjacent rows of 0.4-0.6 times the slit length A. As shown in FIG. 1B the slits 6 are provided in a regular pattern in rows extending in the transverse direction X. Alternatively, the slits may be provided in an irregular pattern.

Figure 1C:
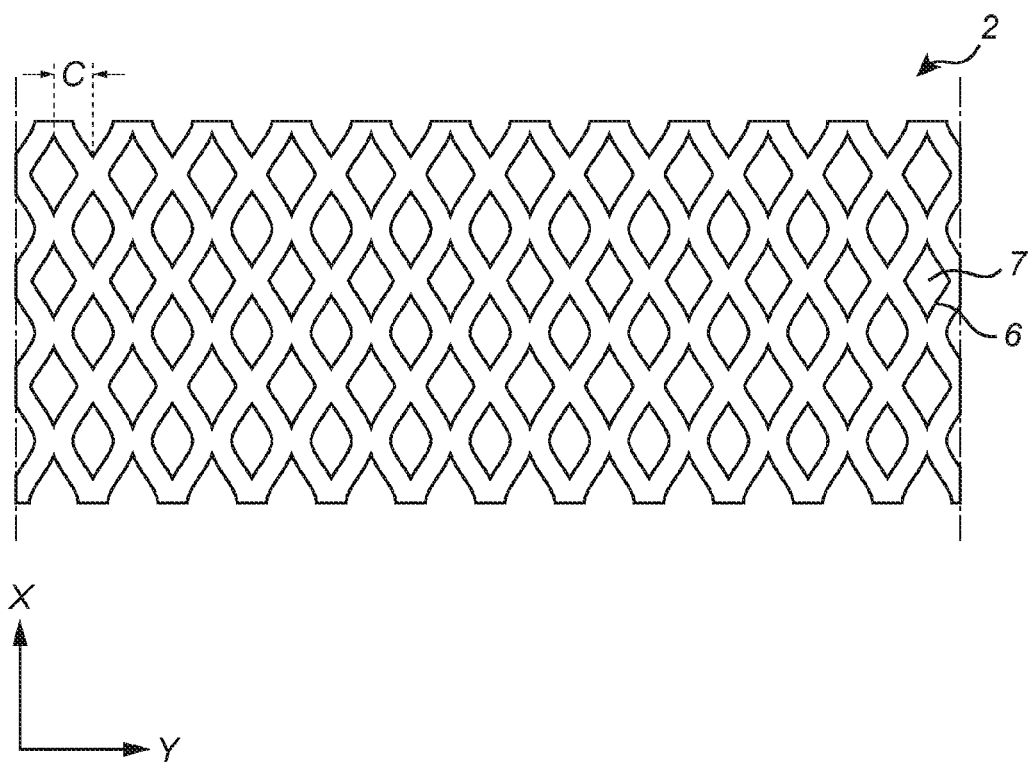
FIG. 1C shows a top view of the first carrier material according to FIG. 1B after it has been expanded, i.e. after the slits have been opened to openings.

FIG. 1C shows a top view of a portion of the first carrier material 2 after it has been expanded, i.e. after the slits 6 have been opened to openings 7.

Figure 2A:
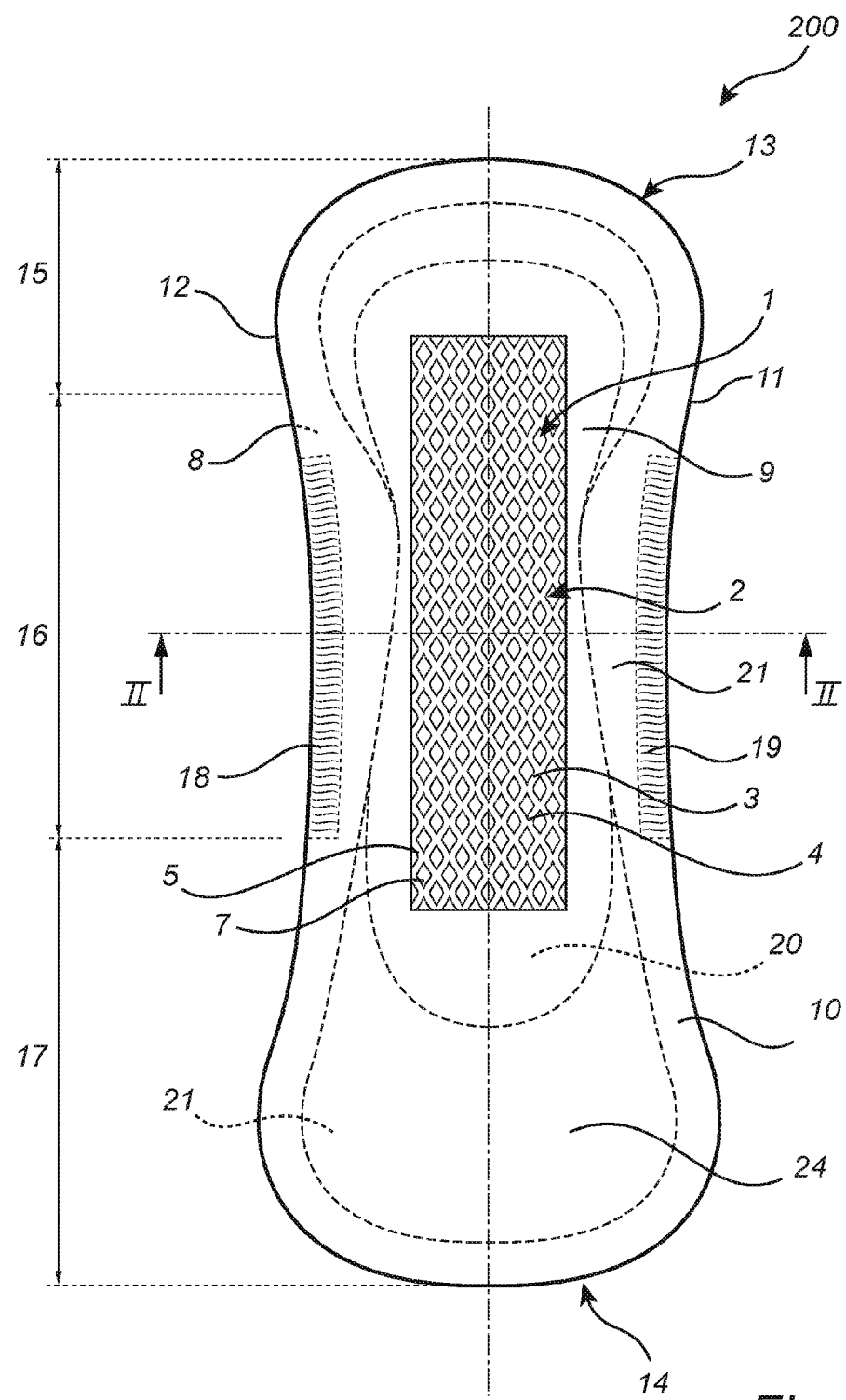
FIG. 2A shows an example of an absorbent product according to an embodiment of the invention, seen from the side which will be facing the user when it is worn.
Figure 2B:
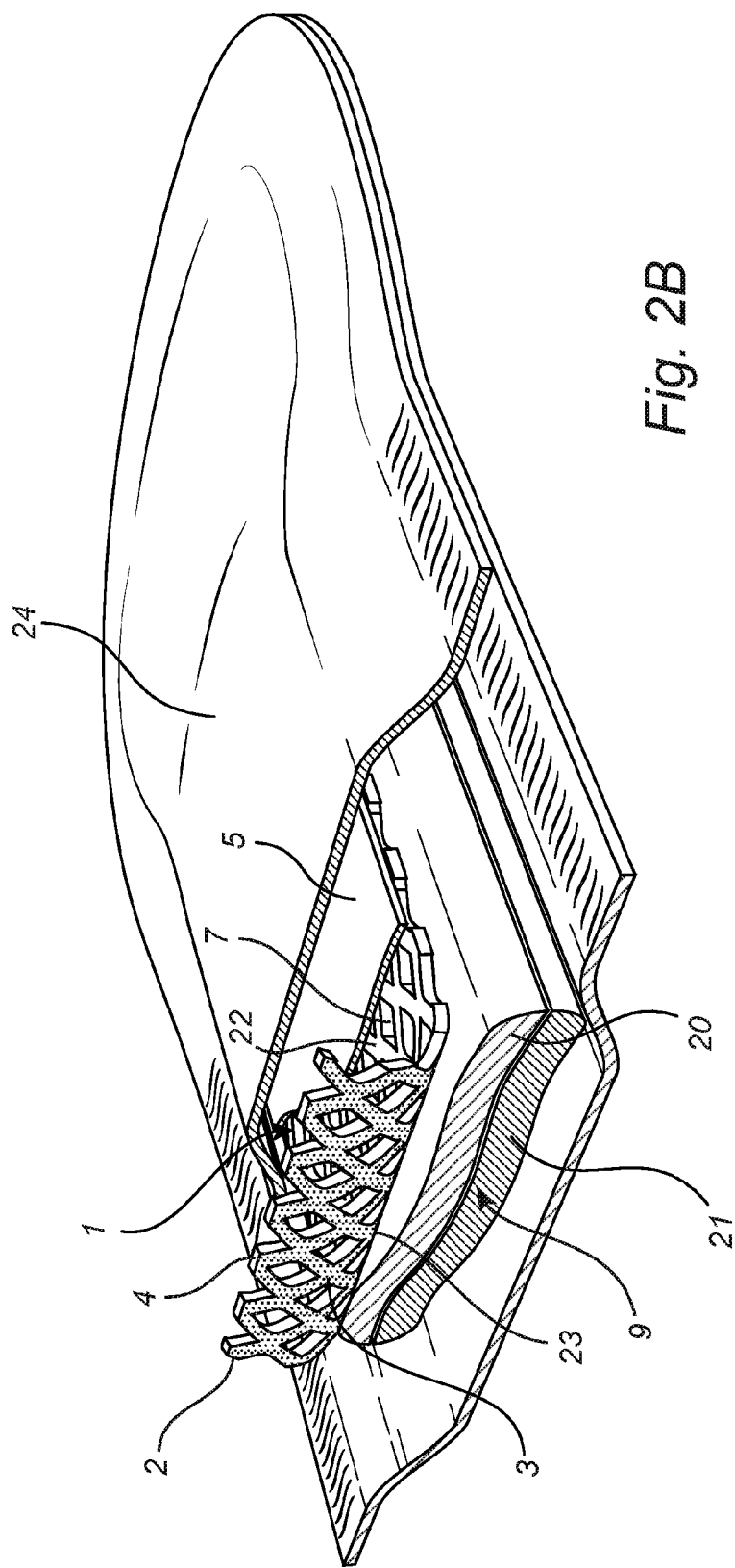
FIG. 2B shows a cross-sectional view of the absorbent product of FIG. 2A, along the line II-II.

The absorbent product shown in FIGS. 2A and 2B is a urine incontinence protector in the form of a pad 200. The pad 200 is seen from the side of the pad that is intended to be facing towards a wearer's body when being worn. The pad 200 comprises a liquid permeable topsheet 24, a liquid impermeable backsheet 8, and an absorbent core 9 enclosed between the topsheet 24 and the backsheet 8, and an odour control material 1 arranged between the topsheet 24 and the absorbent core 9.

The topsheet 24 and the backsheet 8 of the pad 200 extend together laterally outside of the absorbent core 9 along the whole circumference of the absorbent core 9 and is connected to each other in an edge joint 10 around the periphery of the absorbent core 9.

The topsheet 24 consists of any material which is suitable for the purpose, i.e. soft and liquid pervious. Examples of commonly found topsheet 24 materials are nonwoven materials, perforated plastic films, plastic or textile mesh, and fluid permeable foam layers. Laminates consisting of two or more topsheet materials are also commonly employed, as are top sheets consisting of different materials within different parts of the fluid permeable wearer-facing surface.

The backsheet 8 is fluid impermeable. However, backsheet materials that are only fluid repellant may be used particularly in instances where relatively small amounts of urine are expected to be taken up. The backsheet 8 is commonly constituted by a thin, flexible, fluid-impermeable plastic film, but fluid-impermeable nonwoven materials, fluid impermeable foams and fluid impermeable laminates are also contemplated within the scope of the invention. The backsheet 8 may be breathable, implying that air and/or vapor may pass through the backsheet 8. Furthermore, the backsheet 8 may have an outer, garment-facing surface of a textile material such as nonwoven.

The absorbent core 9 may be made up of any suitable absorbent or fluid uptake material as known in the art, such as one or more layers of cellulose fluff pulp, foam, fibre waddings, etc. The absorbent core 9 may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core 9. The fibres may be pulp fibres and the superabsorbent material may be polyacrylate-based particles. An absorbent structure may comprise 40-80% superabsorbents and 60-20% pulp fibres.

The absorbent core 9 may further incorporate components for improving the properties of the absorbent core 9. Some examples of such components are binder fibers, fluid-dispersing materials, wetness indicators etc., as known in the art.

The pad 200 has an elongate, generally rectangular shape when fully extended in all directions. Any suitable shape may be used for the absorbent product, such as hourglass shape, trapezoidal shape, triangular shape an oval shape, etc. The shape of the product of the invention may be symmetrical about a transverse center line through the product, or may be asymmetrical with end portions having differing shapes and/or differing sizes.

The pad 200 has two longitudinal side edges 11, 12 extending generally in the same direction as a longitudinal center line through the absorbent product. Front and rear end edges 13, 14 typically extend transversely to the longitudinal center line at the ends of the absorbent product. The rear end edge 14 is intended to be orientated rearwards during use of the absorbent article, and the front end edge 13 is intended to be facing forwards towards the abdomen of the wearer. The pad 200 has a front end portion 15, a rear end portion 17 and a crotch portion 16 located intermediate the end portions 15, 17. The crotch portion 16 is a portion which is intended to be placed against the crotch of a wearer during use of the product and to constitute the main acquisition area for body fluid that reaches the pad 200.

The pad 200 may further include fastening means for fastening of the absorbent product inside a supporting pant garment, such as a pair of underpants. The fastening means may be in the form of two longitudinally extending bands of pressure sensitive adhesive arranged on the garment-facing surface of the backsheet 8. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

Elastic elements 18, 19 may be arranged along the side edges laterally outside the absorbent core 9. The elastic elements 18, 19 may be bands of elastic material. The elastic elements 18, 19 are optional components of the absorbent product and may be omitted.

The fastening means is optional to the invention and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means may be a mechanical fastener such as hook-type fasteners, clips, press studs, etc. or may be a frictional fastener such as a frictional coating or an open-celled foam. Combinations of different types of fasteners are also conceivable.

The odor control material 1 in FIG. 2A is situated above the absorbent core 9 and beneath and in direct contact with the topsheet 24. However, it is also possible that the absorbent product comprises a liquid acquisition and distribution layer and the odor control material may in such a product be situated between the liquid acquisition and distribution layer and the absorbent core, or between other layers in the product. The absorbent core 9 of the pad 200 comprises a first absorbent layer 20 and a second absorbent layer 21. The odor control material 1 may also be arranged in the absorbent product between the first absorbent layer 20 and the second absorbent layer 21.

The absorbent layers 20, 21 may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibers and superabsorbent material, wherein the ratio of superabsorbent material to fibers may vary in the layer.

The first and second absorbent layers 20, 21 may have any suitable shape, such as an hourglass shape with widened end portions and a narrow portion in the crotch portion, or a rectangular shape. The second absorbent layer 21 is placed below the first absorbent layer 20. The first absorbent layer 20 is smaller than the second absorbent layer 21. The second absorbent layer 21 extends further forward and rearward in the absorbent product than the first absorbent layer 20. However, the absorbent core may also comprise only one single layer or may comprise one or more further absorbent layers. The size of the different layers may also vary, and the absorbent core 9 described in FIGS. 2A and 2B is only one illustration of an absorbent core suitable for the present invention.

The odor control material 1 in the absorbent pad 200 illustrated in FIGS. 2A and 2B has a rectangular shape and may be surrounded in the longitudinal and lateral directions by portions of the absorbent core. Other shapes and configurations for the odor control material 1 may also be used. In FIG. 2B, a cross-sectional view of the absorbent product of FIG. 2A is shown, along the line II-II. So, the pad 200 has a liquid permeable top sheet 24, a liquid impermeable back sheet 8, and an absorbent core 9 enclosed between the top sheet 24 and the back sheet 8 and the odor control material 1 is located between the topsheet 24 and the absorbent core 9. In FIG. 2 B it is also shown that the first carrier material 2 has a first surface 22 and a second opposite surface 23 wherein the first surface 22 is facing the liquid permeable topsheet 24 and the second surface 23 is facing the absorbent core 9. Furthermore, the odor control particles 3 are bonded to the second surface 23 of the first carrier material 2 so that the surface bonded with odor control particles 3 is facing the absorbent core 9. The first carrier material 2 is laminated to a second carrier material 5 in its expanded state so that the first carrier material 2 is fixed to the second carrier material 5 in the form of a reticulated structure with openings 7. The second carrier material 5 is facing is the topsheet 4 and the first carrier material 2 is facing the absorbent core 9.

EXAMPLES

Example 1—Positioning of Odor Control Material in Absorbent Product

A sensory evaluation was performed to investigate how the position of the odor control material in the thickness direction of the product influenced the odor inhibition; close to the backsheet, in the middle of the product between two layers in the absorbent core, or directly below the topsheet.

Tested absorbent products:
1. Incontinence pad without odor control material (reference)
2. Incontinence pad with odor control material directly above the backsheet
3. Incontinence pad with odor control material between layers in the absorbent core
4. Incontinence pad with odor control material directly below the topsheet The incontinence pad had a topsheet, a backsheet and an absorbent core there between. The absorbent core comprised two layers, wherein the first layer was facing the topsheet and the second layer was facing the backsheet. The first layer facing the topsheet had a smaller total surface area in the plane of the pad than the second layer. The odor control material had the same size (surface area) as the first absorbent layer. The first absorbent layer covered about 50% of the total surface of the incontinence pad so therefore also the odor control material covered about 50% of the total surface of the incontinence pad. The odor control material was placed at three different positions in the products; on top of the product, between the absorbent cores and in the bottom of the product. An odor solution containing Diacetyl (250 ng/ml), Dimethyl trisulfide (14 ng/ml) and 3-methyl butanal (40 ng/ml), was added to each product before the odor evaluation took place.

There were 11 panelists. The panelists were asked to judge the odor intensity of the test products and to put a mark on a line scale, labeled from very weak (0) to very strong (1). The relative odor intensity for the reference product without an odor control material was set to 1 on the line scale.

The mean values calculated from the panelists' judgments gave the following results:

| Product | Rel. odor intensity |
|---|---|
| 1. Incontinence pad without odor control material (reference) | 1 |
| 2. Incontinence pad with odor control material directly above the backsheet | 0.9 |
| 3. Incontinence pad with odor control material between layers in the abs. core | 0.6 |
| 4. Incontinence pad with odor control material directly below the topsheet | 0.5 |

The outcome of this sensory evaluation indicates that the placement of the activated carbon matters, less smell when it was placed directly below the topsheet, more when it was placed between the two absorbent cores and most when it was placed in the bottom of the product.

Example 2—Odor Control Particles on One Surface of the Carrier Material Compared to Odor Control Particles on Both Surfaces of the Carrier Material A carrier material has a first surface and an opposite second surface. The odor inhibition has been measured for a carrier material having odor control particles bonded to the first surface as well as to the second surface. The odor control particles were activated carbon. The odor inhibition has also been measured for a carrier material with activated carbon on only the second surface of the carrier material. The odor inhibition has also been measured for an incontinence pad without odor control material.

Tested absorbent products:
1. Incontinence pad without odor control material (reference)
2. Incontinence pad with a foam coated with activated carbon on both surfaces of the foam
3. Incontinence pad with a foam coated with activated carbon on only one surface of the foam For the incontinence pad 2, each surface of the foam was coated with 25 gsm of activated carbon so the total amount of carbon was 50 g/m$^2$. For the incontinence pad 3 where the foam in the absorbent product was coated with activated carbon on only one surface, this surface was coated with 50 g/m$^2$ carbon. Hence, the total amount of carbon was the same for absorbent product 2 and absorbent product 3.

Odor reduction was evaluated in the following way: A cocktail with diacetyl, 3-methylbutanal, DMTS and p-cresol was added to the incontinence pad. The incontinence pad was placed in air-tight glass-chambers, and left for incubation at 35° C. so equilibrium could be reached between the solution and the head space. The head space was sampled by a SPME-fiber (solid phase micro extraction-fiber) followed by analysis with a GC-MS (gas-chromatography-mass spectrometry) system. The individual odor substances were detected and odor reduction was calculated by dividing the peak area for the sample with activated carbon particles by the peak area for the sample without activated carbon particles. Sample with activated carbon particles were only compared to samples without activated carbon particles (reference) where the same batch of odor cocktail has been used, and samples with activated carbon particles and samples without activated carbon particles (reference) was always analysed on the same day.

Result:

| Product | Diacetyl | 3-Metylbutanal | DMTS | p-Cresol |
|---|---|---|---|---|
| 1. | 1 | 1 | 1 | 1 |
| 2. | 0.03 | 0.12 | 0.03 | 0.15 |
| 3. | 0.03 | 0.15 | 0.04 | 0.18 |

No difference in odor reduction could be seen between the incontinence pad 2 having activated carbon particles coated on both surfaces compared to the incontinence pad 3 having activated carbon particles coated only on one surface.

The invention claimed is:
1. Hygienic product comprising an odor control material having a longitudinal direction, a transverse direction and a thickness direction, said hygienic product comprising a liquid permeable topsheet, a liquid impermeable backsheet and an absorbent core enclosed between the top sheet and the back sheet, wherein:
the odor control material is located between the topsheet and the absorbent core and comprises a first carrier material wherein a plurality of odor control particles consisting of activated carbon are bonded to at least one surface of the first carrier material by a binder substance,
the first carrier material in an unexpanded condition has a plurality of transversal slits, and the first carrier material in an expanded condition in the longitudinal direction has a plurality of openings, and
the first carrier material is fixed in the expanded condition in the hygienic product whereby the odor control material is in the form of a reticulated structure,
wherein the hygienic product is an absorbent product, wherein the odor control material comprises a second carrier material laminated to the first carrier material in expanded condition so that the first carrier material is fixed to the second carrier material in expanded condition in the form of a reticulated structure with openings, wherein the second carrier material is a nonwoven material.

2. Hygienic product according to claim 1, wherein the odor control material is fixed in the expanded condition in the hygienic product so that the odor control material covers 5-100% of the total surface area in a horizontal plane of the hygienic product.

3. Hygienic product according to claim 1, wherein the odor control material is fixed in the expanded condition in the hygienic product so that the odor control material covers 5-60% of the total surface area in a horizontal plane of the hygienic product.

4. Hygienic product according to claim 1, wherein the first carrier material is a foam material.

5. Hygienic product according to claim 1, wherein the slits are provided in staggered rows extending in the transverse direction, having a slit length A of 5-20 mm and a slit distance B between the ends of two mutually sequential slits in the staggered row of 0.4-0.6 times the slit length A, and a row distance C between two adjacent rows of 0.4-0.6 times the slit length A.

6. Hygienic product according to claim 5, wherein the slit length A divided with the row distance C is less or equal to 10.

7. Hygienic product according to claim 1, wherein the odor control material also comprises an additive selected from the group of a plasticizer, stabilizer, agent improving dispersibility, pH regulating agent, antimicrobial substance, perfume, surfactant, and scenting substance.

8. Hygienic product according to claim 1, wherein the binder substance is water soluble so it at least partially dissolves when in contact with an aqueous solution.

9. Hygienic product according to claim 1, wherein the first carrier material has a first surface and a second opposite surface wherein the first surface is facing the liquid permeable topsheet and the second surface is facing the absorbent core wherein the odor control particles are bonded to the second surface of the first carrier material so that the surface bonded with odor control particles is facing the absorbent core.

10. Hygienic product according to claim 1, wherein the second carrier material is facing the topsheet and the first carrier material is facing the absorbent core.

11. Method for producing a hygienic product comprising an odor control material having a longitudinal direction, a transverse direction and a thickness direction, said hygienic product comprising a liquid permeable topsheet, a liquid impermeable backsheet and an absorbent core enclosed between the top sheet and the back sheet, wherein the method comprises the following steps:
locating the odor control material between the topsheet and the absorbent core;
providing a first carrier material forming part of the odor control material and having a first surface and a second opposite surface;
bonding a plurality of odor control particles consisting of activated carbon to at least the first surface by means of a binder substance;
providing a plurality of transversal slits in the first carrier material, in an unexpanded condition thereof, so that the first carrier material in an expanded condition in the longitudinal direction has a plurality of openings; and
fixing the first carrier material in the expanded condition in the hygienic product whereby the odor control material is in the form of a reticulated structure, wherein the hygienic product is an absorbent product, wherein the odor control material comprises a second carrier material laminated to the first carrier material in expanded condition so that the first carrier material is fixed to the second carrier material in expanded condition in the form of a reticulated structure with openings, wherein the second carrier material is a nonwoven material.

* * * * *